United States Patent [19]

Ray

[11] Patent Number: 4,654,352

[45] Date of Patent: Mar. 31, 1987

[54] METHOD FOR TREATING DIARRHEA WITH BENZOTHIOPHENE DERIVATIVES

[75] Inventor: Stephen J. Ray, Walmer, England

[73] Assignee: Pfizer Inc., New York, N.Y.

[21] Appl. No.: 750,115

[22] Filed: Jun. 28, 1985

[30] Foreign Application Priority Data

Jul. 10, 1984 [GB] United Kingdom ............... 8417559

[51] Int. Cl.$^4$ ............... A61K 31/38; A61K 31/41; A61K 31/445

[52] U.S. Cl. ............... 514/324; 514/422; 514/443; 546/274; 548/525; 549/51; 549/57

[58] Field of Search ............... 546/274; 548/525, 527; 549/51, 57; 514/324, 342, 422, 443

[56] References Cited

U.S. PATENT DOCUMENTS

| | | | |
|---|---|---|---|
| 3,598,839 | 8/1971 | Kaltenbronn | 314/443 |
| 3,944,672 | 3/1976 | Steinman | 514/443 |
| 4,018,893 | 4/1977 | Steinman | 514/443 |
| 4,137,414 | 1/1979 | Kulka | 514/443 |

*Primary Examiner*—Henry H. Jiles
*Assistant Examiner*—J. G. Mullins
*Attorney, Agent, or Firm*—Charles J. Knuth; Peter C. Richardson; Mark Dryer

[57] ABSTRACT

Compounds of the formula:

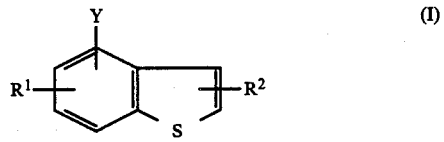

and pharmaceutically-acceptable acid addition salts thereof, wherein $R^1$ is at the 3 or 4 position and is phenyl or phenyl substituted by halo, $(C_1$–$C_4)$alkoxy, or $(C_2$–$C_5)$alkoxycarbonyl; $R^2$ is at the 2 or 7 position and is a group of the formula $X(CH_2)_nNR^3R^4$ where X is —CH=CH— or —$(CH_2)_2$—; n is 1, 2, 3 or 4; and each of $R^3$ and $R^4$ is hydrogen or $(C_1$–$C_4)$alkyl, or $R^3$ and $R^4$ together with the nitrogen atom to which they are attached form a 1-pyrrolidinyl or piperidino group; Y is hydrogen, $(C_1$–$C_4)$alkyl, $(C_1$–$C_4)$alkoxy or $(C_2$–$C_5)$-alkoxycarbonyl at the 4, 5, 6 or 7 position; and wherein $R^2$ is at the 2-position, $R^1$ is at the 3- or 4-position, or alternatively when $R^2$ is at the 7-position, $R^1$ is at the 3-position; are useful for the treatment of diarrhea in humans and animals.

1 Claim, No Drawings

METHOD FOR TREATING DIARRHEA WITH BENZOTHIOPHENE DERIVATIVES

FIELD OF INVENTION

This invention relates to therapeutic agents and in particular to substituted benzothiophene compounds, more particularly a series of 3-phenylbenzo[b]thiophene compounds, which are valuable as antidiarrhoeal agents.

BACKGROUND OF THE INVENTION

Diarrhoea is one of the major causes of morbidity and mortality in the world, and in developing countries it accounts for more infant fatalities than any other single cause. Even in North America and Europe it is a leading reason for death or debilitation among both the young and the elderly. Severe diarrhoea is most commonly caused by an infection of the small intestine; however, the microorganism itself does not invade the intestinal mucosa but produces an enterotoxin which is believed to be responsible for stimulating active electrolyte secretion and consequent fluid loss.

Although the introduction of oral hydration therapy has greatly simplified the treatment of dehydrating diarrhoea, drugs that reduce the rate of fluid loss also have an important role in the management of the condition. One such drug which has recently been identified as a promising antisecretory drug for use in the treatment of dehydrating diarrhoea is chlorpromazine ("Secretary Diarrhea", American Physiological Society (1980), pp 211-218. However, chlorpromazine also has marked effects on the central nervous system at the dosages used, most notably sedation. The present invention provides compounds which are useful in the treatment of diarrhoea but which have significantly reduced sedative effects.

Certain phenylbenzo[b]thiophenes having anti-inflammatory properties are disclosed in U.S. Pat. No. 3,598,839.

Other benzothiophene compounds, useful as antimicrobial agents are disclosed in U.S. Pat. Nos. 3,944,672 and 4,018,893.

U.S. Pat. No. 4,137,414 discloses certain 5-substituted-2-phenylbenzo[b]thiophene-3-alkylamines, useful as neuroleptics or antibacterial agents.

SUMMARY OF THE INVENTION

In accordance with the present invention there is provided a substituted benzothiophene compound, useful as an anti-diarrhoeal agent, having the formula:

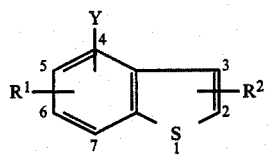

(I)

and pharmaceutically-acceptable acid addition salts thereof, wherein

R$^1$ is at the 3 or 4 position and is phenyl or phenyl substituted by halo, (C$_1$-C$_4$)alkoxy, or (C$_2$-C$_5$)alkoxycarbonyl;

R$^2$ is at the 2 or 7 position and is a group of the formula:

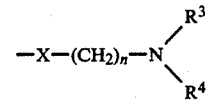

wherein
X is —CH=CH— or —(CH$_2$)$_2$—; n is 1, 2, 3 or 4; and each of R$^3$ and R$^4$ is hydrogen or (C$_1$-C$_4$)alkyl, or R$^3$ and R$^4$ together with the nitrogen atom to which they are attached form a 1-pyrrolidinyl or piperidino group;

Y is hydrogen, (C$_1$-C$_4$)alkyl, (C$_1$-C$_4$)alkoxy or (C$_2$-C$_5$)alkoxycarbonyl at the 4, 5, 6 or 7 position; and wherein when R$^2$ is at the 2-position, R$^1$ is at the 3- or 4-position, or alternatively when R$^2$ is at the 7-position, R$^1$ is at the 3-position.

The invention also provides a pharmaceutical composition containing a compound of the formula (I) or a pharmaceutically-acceptable acid addition salt thereof, in admixture with a pharmaceutically-acceptable diluent or carrier.

The invention further provides a method for the prevention or treatment of diarrhoea in a human or animal patient, which comprises administering to the patient an anti-diarrhoeal effective amount of a compound of the formula (I) or a pharmaceutically-acceptable acid addition salt thereof.

In the above definitions halo means fluoro, chloro, bromo or iodo. Alkyl groups containing three or more carbon atoms may be straight or branched chain.

One particular and preferred group of compounds are the compounds of formula (I) wherein R$^1$ is at the 3-position and R$^2$ at the 2-position. Also preferred are compounds wherein X is (CH$_2$)$_n$ especially when n is 2. A preferred value for R$^3$ and R$^4$ is methyl. R$^1$ is preferably phenyl.

Thus one particular and preferred compound of the invention is 2-(4-dimethylaminobutyl)-3-phenylbenzo[b]thiophene.

DETAILED DESCRIPTION OF THE INVENTION

The compounds of the invention can be prepared from an appropriate aryl-substituted-benzo[b]thiophenecarboxaldehyde.

The process is illustrated by the following reaction scheme where R$^1$ is shown at the 3-position and R$^2$ is at the 2-position:

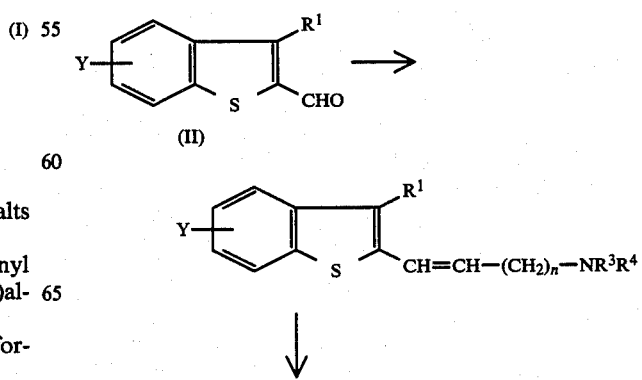

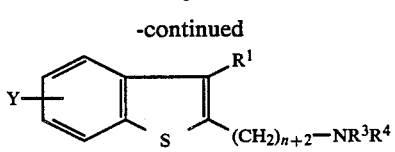

In the first step, compounds of the formula (I) wherein X is —CH=CH— are prepared from the aldehyde (II) by a Wittig reaction using the ylide generated from the appropriate $R^3,R^4$-substituted-aminoalkyltriphenylphosphonium halide by reaction with butyllithium.

The reaction is generally performed by adding a solution of butyllithium to a cooled solution of the phosphonium halide, generally the chloride, in an organic solvent, for example tetrahydrofuran. After a few minutes the carboxaldehyde (II) is added. A period of several hours at room temperature is generally sufficient to ensure completion of the reaction and the product is then isolated by conventional procedures.

The compounds of formula (I) wherein X is —(CH$_2$)$_2$— are readily prepared from the corresponding compounds wherein X is —CH=CH— by catalytic hydrogenation. The reaction is typically performed at a pressure of 60 p.s.i. (4.2 bar) and room temperature in the presence of platinum oxide or palladium on charcoal catalyst and is generally complete after a few hours.

The compounds of formula (I) wherein $R^1$ is at the 4-position and $R^2$ at the 2-position and the compounds of formula (I) wherein $R^1$ is at the 3-position and $R^2$ at the 7-position are prepared in an exactly analogous manner starting with the appropriate 4-aryl-benzo[b]-thiophene-2-carboxaldehyde or 3-aryl-benzo[b]thiophene-7-carboxaldehyde respectively.

As a variant of this process, especially useful for preparing compounds of the formula (I) wherein $R^3$ and $R^4$ are both hydrogen and n is 3 or 4, the aldehyde (II) is reacted with the ylide generated from a cyanoalkyltriphenylphosphonium halide to give a cyanoalkyl olefin; reduction of this by catalytic hydrogenation followed by reduction with lithium aluminium hydride gives the corresponding aminoalkyl product.

The free amine wherein $R^3$ and $R^4$ are both hydrogen may also be alkylated by conventional means to give the corresponding compounds wherein $R^3$ and $R^4$ are $C_1$-$C_4$ alkyl. Thus, for example methylation with a mixture of formic acid and formalin yields the dimethylamino derivative wherein $R^3$ and $R^4$ are methyl.

The starting 3-aryl-benzo[b]thiophene-2-carboxaldehydes of formula (II) and 4-aryl-benzo[b]thiophene-2-carboxaldehydes are generally known compounds. They are conveniently prepared from the corresponding 3- or 4-aryl-benzo[b]thiophene by reaction with butyllithium followed by addition of dimethylformamide. The 3-aryl-benzo[b]thiophene-7-carboxaldehydes are prepared from the corresponding 7-methyl compound, for example by bromination with N-bromosuccinimide followed by a Sommelet reaction. The aminoalkyltriphenylphosphonium halides are generally known compounds prepared in accordance with literature precedents, for example, by reaction of a bromoalkyltriphenylphosphonium halide with the appropriate amine $HNR^3R^4$.

Acids from which pharmaceutically acceptable addition salts of the compounds of the invention can be prepared are those which form non-toxic addition salts containing pharmaceutically acceptable anions, such as the hydrochloride, hydrobromide, hydroiodide, sulphate or bisulphate, phosphate or acid phosphate, acetate, maleate, fumarate, lactate, tartrate, citrate, gluconate, saccharate and p-toluene sulphonate salts.

The compounds of the invention are valuable for the treatment of diarrhoea in both humans and animals, especially for the treatment of severe forms of diarrhoea of bacterial origin, for example, associated with *E.coli* infections in humans and enteritis in pigs. The compounds are also of value in treating milder forms of the condition such as travellers' diarrhoea.

The activity of the compounds is assessed using a test procedure based on that described by Giannella in Infection and Immunity 1976, 14, 95–99, in which the ability of the compounds to inhibit the intestinal secretion induced by administration of an enterotoxin is measured in suckling mice. In practice a group of mice are given an oral dose of a heat stable toxin produced by *E.coli* as described by Staples et. al., J. Biol. Chem., 1980, 255, 4716. This induces intestinal fluid secretion and causes an increase in gut weight relative to that of the remaining carcass. A further group of mice are dosed with the toxin followed by the compound under investigation at various dose levels. After 2½ hours at 23° C. the mice are killed and the weight of the gut measured as a proportion of the remaining carcass. The ED$_{50}$ value is recorded as the dose of compound which is able to reduce the level of enterotoxin induced secretion to 50% of that observed in untreated animals. The test can also be performed using a heat labile enterotoxin, produced for example by *Vibrio cholerae* as described by Kusama and Craig, Infection and Immunity, 1970, 1, 80.

For human use, the anti-diarrhoeal compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral administration to human patients, the daily dosage level of the anti-diarrhoeal compounds of the formula (I) will be from 1–40 mg./kg., preferably 2–10 mg./kg. (in divided doses). Thus tablets or capsules of the compounds can be expected to contain from 5 mg to 25 mg of active compound for administration singly or two or more at a time as appropriate. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

The compounds may be administered together with other agents, for example antibiotics, and with concurrent hydration therapy if appropriate.

The preparation of the compounds of the formula (I) is illustrated by the following Examples.

EXAMPLE 1

2-(4-Dimethylaminobut-1-enyl)-3-phenylbenzo[b]thiophene oxalate

A solution of butyllithium (75 ml of 1.6M solution in hexane; 0.12 mole) was added to a stirred slurry of 3-dimethylaminopropyltriphenylphosphonium chloride (53.7 g; 0.14 mole) in tetrahydrofuran (180 ml) at 0° C. The resulting mixture was stirred for 30 minutes at 0° C. and a solution of 3-phenylbenzo[b]thiophene-2-carboxaldehyde (16.9 g; 0.071 mole) in tetrahydrofuran (20 ml) was then added in a stream. The mixture was allowed to warm to room temperature and stirred at this temperature overnight. The reaction was quenched by the addition of water, the tetrahydrofuran removed under reduced pressure and the resulting oil extracted into diethyl ether. The ethereal solution was extracted with dilute hydrochloric acid (0.5M), the acid extract was made basic by the addition of 2M sodium hydroxide solution and the resulting oil extracted into diethyl ether. The ethereal extract was dried over potassium carbonate and treated with excess oxalic acid in diethyl ether. The resulting precipitate was collected and dried to yield the desired product as the oxalate salt (26.1 g). Recrystallisation from isopropyl alcohol gave the pure product as a mixture of cis and trans isomers. m.p. 156°–160° C.

Found: C,65.56; H,5.89; N,3.65; S,7.77. $C_{20}H_{21}NS:C_2H_2O_4 \cdot \frac{1}{4}H_2O$ requires C 65.74; H,5.89; N,3.49; S,7.96%.

EXAMPLE 2

2-(4-Dimethylaminobutyl)-3-phenylbenzo[b]thiophene p-toluene sulphonate

A solution of 2-(4-dimethylaminobut-1-enyl)-3-phenylbenzo[b]thiophene oxalate (21.6 g, 0.065 mole) in methanol (250 ml) and water (10 ml) was hydrogenated at a pressure of 60 p.s.i at room temperature for 4 hours in the presence of platinum oxide (1 g). At the end of this time the catalyst was removed by filtration and the solvent evaporated. The resulting solid was dissolved in water, the pH adjusted to 10 with 2M sodium hydroxide solution and the resulting oil extracted into diethyl ether. The ethereal extract was dried over potassium carbonate, treated with decolouring charcoal and filtered. A solution of excess p-tolulenesulphonic acid in diethyl ether was added to precipitate the product as the p-toluenesulphonate salt. Recrystallisation from ethyl acetate gave the title product (21.4 g) m.p. 75°–77° C.

Found: C, 67.12; H, 6.62; N, 2.85. $C_{20}H_{23}NS:C_7H_8O_3S$ requires C, 67.34; H, 6.49; N 2.91%.

EXAMPLE 3

Cis/trans 2-(3-Dimethylaminoprop-1-enyl)-3-phenylbenzo[b]thiophene oxalate was prepared as described in Example 1 starting with 2-dimethylaminoethyltriphenylphosphonium chloride. The product had m.p. 154°–156° C. (from isopropyl alcohol).

Found: C, 65.44; H, 5.51; N, 3.83. $C_{19}H_{19}NS:C_2H_2O_4$ requires C, 65.78; H, 5.52; N, 3.65%.

EXAMPLE 4

2-(3-Dimethylaminopropyl)-3-phenylbenzo[b]thiophene oxalate was prepared by hydrogenation of the product of Example 3 following the procedure described in Example 2. The product had m.p. 164°–168° C. (from isopropyl alcohol).

Found: C, 65.09; H, 6.13; N, 3.75. $C_{19}H_{21}NS:C_2H_2O_4$ requires C, 65.44; H, 6.01; N, 3.63%.

EXAMPLES 5–12

The following compounds were prepared following the general procedures of Examples 1 to 4 starting with the appropriate 3-aryl-benzothiophene-2-carboxaldehyde (II). The compounds were isolated as their oxalate salts.

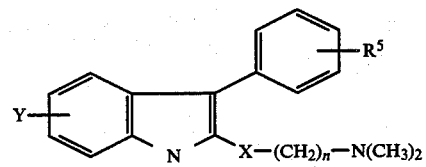

| Example No. | $R^5$ | X | Y | n | m.p. °C. | Analysis % (Theoretical in Brackets) C | H | N |
|---|---|---|---|---|---|---|---|---|
| 5 | 4-CH$_3$O | (CH$_2$)$_2$ | H | 2 | 134–136 | 64.38 (64.37 | 6.24 6.34 | 3.52 3.26) |
| 6 | 4-CO$_2$CH$_3$ | (CH$_2$)$_2$ | H | 2 | 142–143 | 63.06 (63.01 | 5.97 5.95 | 3.02 3.06) |
| 7 | 4-F | (CH$_2$)$_2$ | H | 2 | 161–162 | 63.67 (63.30 | 5.67 5.80 | 3.30 3.36) |
| 8 | 2-Cl | (CH$_2$)$_2$ | H | 2 | 162–163 | 61.10 (60.90 | 5.59 5.58 | 3.20 3.23) |
| 9 | H | (CH$_2$)$_2$ | 5-CH$_3$ | 2 | 140–142 | 66.48 (66.80 | 6.55 6.58 | 3.61 3.39) |
| 10 | H | (CH$_2$)$_2$ | 7-CH$_3$ | 1 | 162–166 | 66.18 (66.15 | 6.34 6.31 | 3.57 3.51) |
| 11 | H | (CH$_2$)$_2$ | 7-CH$_3$ | 2 | 153–156 | 66.47 (66.80 | 6.67 6.58 | 3.68 3.39) |
| 12 | H | (CH$_2$)$_2$ | 5-CO$_2$CH$_3$ | 2 | 128–134 hemihydrate | 62.06 (61.79 | 6.35 6.03 | 3.08 3.00) |

EXAMPLE 13

2-(5-Aminopentyl)-3-phenylbenzo[b]thiophene

1.

2-(4-cyanobut-1-enyl)-3-phenylbenzo[b]thiophene

A solution of lithium diisopropylamide (27 mmole in 10 ml tetrahydrofuran) was added dropwise to a stirred slurry of 3-cyanopropyl-triphenylphosphonium bromide (12.3 g; 30 mmole) in tetrahydrofuran (65 ml) at −10° C. The mixture was maintained at this temperature for 30 minutes and a solution of 3-phenylbenzo[b]thiophene-2-carboxaldehyde (4.8 g; 20 mmole) in tetrahydrofuran (10 ml) was added and the mixture stirred at room temperature for 1.5 hours. The reaction was quenched by pouring into water (100 ml) and extracting with diethyl ether (3×70 ml). The combined ethereal extracts were dried over magnesium sulphate and concentrated under reduced pressure. The resulting product was chromatographed on silica gel eluting with a mixture of methylene chloride and hexane to give the desired cyano-olefin (4.1 g).

2.

2-(4-Cyanobutyl)-3-phenylbenzo[b]thiophene

The cyano-olefin above (4.0 g; 13.8 mmole) was dissolved in isopropyl alcohol (100 ml) and hydrogenated over 10% palladium on charcoal catalyst for 12 hours at 60 p.s.i. (4.2 bar) and 40° C. The catalyst was removed by filtration and the solution concentrated under reduced pressure to yield 2-(4-cyanobutyl)-3-phenylbenzo[b]thiophene (3.5 g).

3.

2-(5-Aminopentyl)-3-phenylbenzo[b]thiophene

A solution of the product from 2 above (1.0 g, 3.43 mmole) in diethyl ether (10 ml) was added dropwise to a stirred suspension of lithium aluminium hydride (0.5 g, 13.2 mmole) in diethyl ether (20 ml) and the mixture stirred overnight at room temperature. The mixture was subsequently treated cautiously with water (0.5 ml) followed by 50% potassium hydroxide solution (0.5 ml). The resulting solids were removed by filtration and washed with diethyl ether. The combined organic fractions were dried over magnesium sulphate and concentrated to dryness to yield the desired amine as an oil (0.89 g). A sample was converted to the maleate salt which was recrystallised from a mixture of isopropyl alcohol and diisopropyl ether. m.p. 102°–105° C.

Found: C, 66.93; H, 6.08; N, 3.32. $C_{19}H_{21}NS$: $C_4H_4O_4$ requires C, 67.14; H, 6.13; N, 3.41%.

EXAMPLE 14

2-(5-Dimethylaminopentyl)-3-phenylbenzo[b]thiophene oxalate

A mixture of 2-(5-aminopentyl)-3-phenylbenzo[b]thiophene (0.35 g, 1.18 mmole), formic acid (5 ml) and formalin (5 ml) was heated on a steam bath for 4 hours. The reaction mixture was cooled and poured into water (20 ml). The pH was adjusted to 10 by the addition of sodium hydroxide solution and the resulting oil was extracted into diethyl ether (2×30 ml). The ethereal extracts were washed with water, dried over magnesium sulphate and concentrated under reduced pressure. The product was taken up in a little diethyl ether and precipitated as the oxalate salt by adding an ethereal solution of oxalic acid. The product was collected by filtration and recrystallised from a mixture of isopropyl alcohol and diisopropyl ether to give the title product (0.1 g). m.p. 138°–141° C.

Found: C, 67.10; H, 6.59; N, 3.34. $C_{21}H_{25}NS$: $C_2H_2O_4$ requires C, 66.84; H, 6.59; N, 3.39%.

EXAMPLE 15

2-(4-Piperidinobut-1-enyl)-3-phenylbenzo[b]thiophene

The procedure of Example 1 was followed starting with 3-phenylbenzo[b]thiophen-2-carboxaldehyde (2.4 g, 10 mmole) but reacting with the ylide generated from 3-piperidinopropyltriphenylphosphonium bromide (7.02 g, 15 mmole) by reaction with butyllithium (7.5 ml, 1.6 molar; 12 mmoles). The product was isolated as the hydrochloride salt as a mixture of cis and trans isomers (2.1 g) m.p. 200°–202° C.

Found: C, 72.29; H, 6.99; N, 3.74. $C_{23}H_{25}NS.HCl$ requires C, 71.94; H, 6.82; N, 3.65%.

EXAMPLE 16

2-(4-Piperidinobutyl)-3-phenylbenzo[b]thiophene hydrochloride

Catalytic reduction of 2-(4-piperidinobut-1-enyl)-3-phenylbenzo[b]thiophene hydrochloride (2.0 g) by the procedure of Example 2 gave the title compound which was isolated as the hydrochloride salt (1.9 g) from isopropyl alcohol and diisopropyl ether. m.p. 156°–157° C.

Found: C, 69.85; H, 7.21; N, 3.36. $C_{23}H_{27}NS.HCl.\frac{1}{2}H_2O$ requires C, 69.93; H, 7.40; N, 3.55%.

EXAMPLES 17–20

The following compounds were prepared from 4-phenylbenzo[b]thiophene-2-carboxaldehyde by reaction with the appropriate aminoalkyltriphenylphosphonium ylide followed by reduction according to the general procedures of Examples 1 and 2.

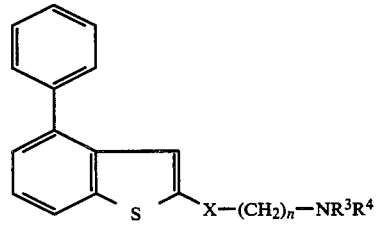

| Example No. | X | n | NR³R⁴ | m.p. °C. | Analysis % (Theoretical in Brackets) | | |
|---|---|---|---|---|---|---|---|
| | | | | | C | H | N |
| 17 | CH=CH | 2 | N(CH₃)₂ | 108–111[a] | 67.34 (67.34 | 5.94 6.00 | 3.41 3.27) |
| 18 | (CH₂)₂ | 2 | N(CH₃)₂ | 148–150[b] | 65.51 (65.42 | 6.42 6.36 | 3.35 3.47) |
| 19 | CH=CH | 1 |  | 114–116[c] | 68.94 68.81 | 5.73 5.79 | 3.26 3.22) |

-continued

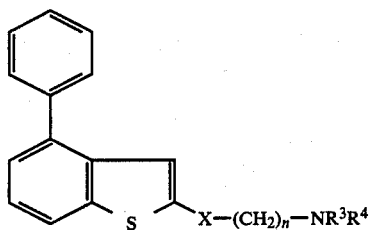

| Example No. | X | n | NR³R⁴ | m.p. °C. | Analysis % (Theoretical in Brackets) | | |
|---|---|---|---|---|---|---|---|
| | | | | | C | H | N |
| 20 | (CH₂)₂ | 1 |  | 181[d] (dec) | 63.86 (63.66 | 6.04 6.39 | 3.04 3.24) |

[a]maleate: ¼ H₂O from isopropyl alcohol/diethylether.
[b]oxalate: ¼ H₂O from isopropyl alcohol/diethylether.
[c]maleate from isopropyl alcohol/diisopropyl ether.
[d]oxalate: ¼ H₂O from methanol.

EXAMPLE 21

7-(4-Dimethylaminoprop-1-enyl)-3-phenylbenzo[b]thiophene hydrochloride (a) 7-Bromomethyl-3-phenylbenzo[b]thiophene (13.5 g; 44.6 mmole) was added to a solution of hexamine (14.0 g; 0.1 mole) in a mixture of acetic acid (50 ml) and water (25 ml) and the mixture refluxed with stirring for 3.5 hours. Concentrated hydrochloric acid (25 ml) was added and the mixture refluxed for a further 20 minutes. The solution was cooled, poured into water and extracted with diethyl ether. The combined ether extracts were dried over magnesium sulphate and evaporated. The crude product was purified by column chromatography on silica eluting with a mixture of methylene chloride and hexane. The relevant fractions were combined and evaporated to yield 3-phenylbenzo[b]thiophene-7-carboxaldehyde as an oil. (4.9 g).

(b) The product from (a) was treated with the ylide prepared from 2-dimethylaminoethyltriphenylphosphonium chloride and butyllithium following the procedure of Example 1 to yield the title compound which was isolated as its hydrochloride salt and recrystallised from isopropyl alcohol. m.p. 193°–196° C.

Found: C, 68.98; H, 5.92; N, 4.63. C₁₉H₁₉NS:HCl requires C, 69.19; H, 6.11; N, 4.25%.

EXAMPLES 22–24

The following compounds were prepared from 3-phenylbenzo[b]thiophene-7-carboxaldehyde and the appropriate aminoalkyltriphenylphosphonium ylide followed by catalytic reduction according to the general procedures of Examples 1 to 4 respectively.

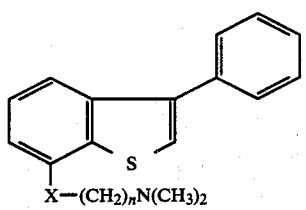

| Example No. | X | n | m.p. °C. | Analysis % (Theoretical in Brackets) | | |
|---|---|---|---|---|---|---|
| | | | | C | H | N |
| 22 | CH=CH | 2 | 146–150[a] | 68.64 (68.94) | 6.41 6.51 | 4.29 4.02) |
| 23 | (CH₂)₂ | 1 | 133–137[b] | 67.14 (67.13) | 6.13 6.12 | 3.31 3.40) |
| 24 | (CH₂)₂ | 2 | 99–101[b] | 67.71 (67.74) | 6.48 6.40 | 3.57 3.29) |

[a]Hydrochloride: ¼ H₂O from isopropyl alcohol/acetone.
[b]Maleate from isopropyl alcohol/diisopropylether.

PREPARATION 1

Preparation of 3-phenylbenzo[b]thiophene-2-carboxaldehyde

Butyllithium (62.5 ml of 1.6M solution in hexane, 0.1 mole) was added dropwise to a stirred solution of 3-phenylbenzo[b]thiophene (21.0 g, 0.1 mole) in tetrahydrofuran (150 ml) at −70° C. The solution was stirred at −70° C. for 30 minutes and dimethylformamide (10 ml, 0.13 mole) was added. The resulting mixture was stirred at −70° C. for 30 minutes and then allowed to warm to ambient temperature. After a further hour the reaction was quenched by the addition of dilute hydrochloric acid (100 ml, 2M) and the tetrahydrofuran removed under reduced pressure. The resulting oil was extracted into diethyl ether, the ethereal extract washed with water, dried over potassium carbonate and concentrated.

The crude product was crystallised from a mixture of diethyl ether and hexane to give the title compound (16.9 g). m.p. 86°–89° C.

PREPARATION 2

3-(4-Methoxyphenyl)-benzo[b]thiophene

A solution of butyl lithium in hexane (15 ml, 1.6M; 24 mmole) was added to a stirred solution of 3-bromobenzothiophene (5 g, 23.5 mmole) in diethyl ether (70 ml) at −78° C. The mixture was stirred at −75° C. for 30 minutes and then a solution of anhydrous zinc chloride (3.2 g, 23.5 mmoles) in diethyl ether (70 ml) was added. The mixture was maintained at −70° C. for a further 30 minutes and 4-iodoanisole (5.2 g, 22.2 mmole) and tetrakis triphenylphosphine palladium (0) (1.4 g, 1.2 mmole) were then added. The reaction mixture was allowed to warm to room temperature and after one hour 2N hydrochloric acid (50 ml) was added. The organic phase was separated, washed with water (2×50 ml) and dried. The solvent was evaporated and the crude product chromatographed on silica to obtain the desired product (2.7 g).

The compound was converted to its 2-carboxaldehyde by the procedure of Preparation 1.

Other 3-aryl-benzo[b]thiophene-2-carboxaldehydes were obtained in a similar manner but lithium diethylamide was used instead of butyl lithium in the preparation of the methoxycarbonyl-phenyl, fluorophenyl and chlorophenyl derivatives.

PREPARATION 3

5-Methoxycarbonyl-3-phenyl-benzo[b]thiophene-2-carboxaldehyde

A solution of 5-bromo-3-phenyl-benzo[b]thiophene-2-carboxaldehyde (15.8 g, 50 mmole), para-toluene sulphonic acid (0.15 g) and ethylene glycol (30) in toluene (150 ml) was refluxed for 2 hours with continuous removal of water using a Dean and Stark apparatus, followed by soxhlet extraction with molecular sieves for 16 hours. The resulting solution was cooled, diluted with diethyl ether (150 ml), washed with sodium bicarbonate solution and water, dried over magnesium sulphate and concentrated under vacuum. The resulting gum was triturated with a mixture of diethyl ether and petrol to give the acetal as a white solid (15.6 g) m.p. 99°–102° C.

A solution of this product (6.3 g, 17.4 mmole) in tetrahydrofuran (40 ml) was treated at −40° C. with a solution of n-butyl lithium (12.0 ml, 1.6M; 19.2 mmole). After stirring at −40° C. for one hour the mixture was cooled to −75° C. and poured onto solid carbon dioxide (30 g). When all the carbon dioxide had vapourised, sufficient water was added to dissolve all the solid matter (50 ml) and the pH of the solution was adjusted to 9 by the addition of 1N sodium hydroxide solution and the mixture was washed with diethyl ether (2×50 ml). Dimethylsulphate (13.3 g, 0.105 mole) was added to the resulting aqueous solution over 2.5 hours, the pH being maintained at 8–9 by the addition of dilute sodium hydroxide solution. The mixture was stirred overnight at room temperature and then extracted with diethyl ether (2×50 ml). The ethereal extracts were washed with sodium bicarbonate solution (30 ml), water (30 ml), dried and evaporated to dryness. Trituration of this solid with a mixture of diethyl ether and hexane yielded the 5-methoxycarbonyl-2-acetal (1.86 g) m.p. 118°–122° C. The mother liquors were evaporated to dryness and the product dissolved in methanol (50 ml) and water (5 ml). Concentrated hydrochloric acid (0.2 ml) was added and the solution refluxed briefly and allowed to stand at room temperature for 4 hours. The methanol was removed under reduced pressure and the resulting gum partitioned between methylene chloride and aqueous sodium bicarbonate solution. The organic phase was separated, dried over sodium carbonate and evaporated. Trituration with a mixture of diethyl ether and hexane gave the desired title aldehyde (1.7 g), m.p. 185°–187° C.

I claim:

1. A method for the prevention or treatment of diarrhoea in a patient, which comprises administering to the patient an anti-diarrheal effective amount of a substituted benzothiophene compound having the formula:

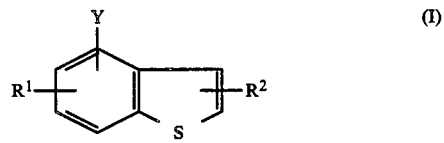

or a pharmaceutically-acceptable acid addition salt thereof, wherein $R^1$ is at the 3 or 4 position and is phenyl or phenyl substituted by halo, $(C_1-C_4)$alkoxy, or $(C_2-C_5)$alkoxy carbonyl;

$R^2$ is at the 2 or 7 position and is a group of the formula:

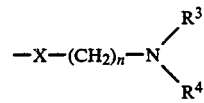

wherein X is —CH=CH— or —$(CH_2)_2$—; n is 1, 2, 3 or 4; and each of $R^3$ and $R^4$ is hydrogen or $(C_1-C_4)$alkyl, or $R^3$ and $R^4$ together with the nitrogen atom to which they are attached form a 1-pyrrolidinyl or piperidino group;

Y is hydrogen, $(C_1-C_4)$alkyl, $(C_1-C_4)$alkoxy or $(C_2-C_5)$alkoxycarbonyl at the 4, 5, 6 or 7 position; and wherein $R^2$ is at the 2-position, $R^1$ is at the 3- or 4-position, or alternatively when $R^2$ is at the 7-position, $R^1$ is at the 3-position.

* * * * *